(12) United States Patent
Doi et al.

(10) Patent No.: US 9,307,916 B2
(45) Date of Patent: Apr. 12, 2016

(54) ELECTRONIC SPHYGMOMANOMETER

(75) Inventors: Ryosuke Doi, Kyoto (JP); Takanori Nishioka, Nagaokakyo (JP); Kohei Takeoka, Kyoto (JP); Yukiya Sawanoi, Nara (JP); Izumi Hachimaru, Kyoto (JP); Masataka Yanagase, Osaka (JP); Kenichi Horibata, Kyoto (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 429 days.

(21) Appl. No.: 13/470,519

(22) Filed: May 14, 2012

(65) Prior Publication Data

US 2012/0226171 A1    Sep. 6, 2012

Related U.S. Application Data

(63) Continuation of application No. PCT/JP2010/070037, filed on Nov. 10, 2010.

(30) Foreign Application Priority Data

Nov. 13, 2009    (JP) .................................. 2009-259919

(51) Int. Cl.
*A61B 5/02* (2006.01)
*A61B 5/022* (2006.01)
*A61B 5/021* (2006.01)
*A61B 5/00* (2006.01)

(52) U.S. Cl.
CPC ............. *A61B 5/022* (2013.01); *A61B 5/02141* (2013.01); *A61B 5/6824* (2013.01)

(58) Field of Classification Search
USPC .................................................. 600/480–515
See application file for complete search history.

(56) References Cited

U.S. PATENT DOCUMENTS

| | | | | |
|---|---|---|---|---|
| 4,953,557 A | * | 9/1990 | Frankenreiter et al. | 600/493 |
| 5,220,925 A | * | 6/1993 | Hishida | 600/493 |
| 6,041,817 A | * | 3/2000 | Guertin | 137/565.23 |
| 7,594,892 B2 | | 9/2009 | Cen et al. | |
| 2002/0087153 A1 | * | 7/2002 | Roschak et al. | 606/27 |

FOREIGN PATENT DOCUMENTS

| | | |
|---|---|---|
| JP | 02-019133 A | 1/1990 |
| JP | 03-060635 A | 3/1991 |
| JP | 07-051233 A | 2/1995 |
| JP | 07-163531 A | 6/1995 |
| JP | 3163340 U | 9/2010 |

OTHER PUBLICATIONS

Patent Abstracts of Japan, Publication No. 07-051233, publication date Feb. 28, 1995 (1 page).

(Continued)

*Primary Examiner* — Michael Kahelin
*Assistant Examiner* — Mitchell E Alter
(74) *Attorney, Agent, or Firm* — Osha Liang LLP

(57) ABSTRACT

In an electronic sphygmomanometer, the thickness of the second connection tube is set to be lower than the thickness of the first connection tube, and therefore, even if error has occurred in the structural dimensions of the pressure sensor air tube, the error can be absorbed as a result of the second connection tube extending/contracting. It is therefore possible to provide an electronic sphygmomanometer that includes, in a structure in which a pressure sensor used in the electronic sphygmomanometer is disposed, a peripheral structure for the pressure sensor that can improve the reliability of blood pressure measurement values.

2 Claims, 9 Drawing Sheets

(56) References Cited

OTHER PUBLICATIONS

Patent Abstracts of Japan, Publication No. 02-019133, publication date Jan. 23, 1990 (1 page).
Patent Abstracts of Japan, Publication No. 03-060635, publication date Mar. 15, 1991 (1 page).
Patent Abstracts of Japan, Publication No. 07-163531, publication date Jun. 27, 1995 (1 page).

International Search Report issued in PCT/JP2010/070037 mailed on Dec. 7, 2010, with English translation thereof, 4 pages.

* cited by examiner

ELECTRONIC SPHYGMOMANOMETER

TECHNICAL FIELD

This invention relates to electronic sphygmomanometers, and particularly relates to electronic sphygmomanometers that improve the reliability of blood pressure measurement values.

BACKGROUND ART

Blood pressure is one index for analyzing cardiovascular disease. Performing a risk analysis for cardiovascular disease based on blood pressure is effective in preventing cardiovascular-related conditions such as stroke, heart failure, and myocardial infarction. In particular, morning hypertension, in which the blood pressure rises in the early morning, is related to heart disease, stroke, and the like. Furthermore, among morning hypertension symptoms, the symptom called "morning surge", in which the blood pressure rapidly rises within one hour to one and a half hours after waking up, has been found to have a causal relationship with stroke. Accordingly, understanding the interrelationship between time (lifestyle) and changes in blood pressure is useful in risk analysis for cardiovascular-related conditions. It is therefore necessary to continuously measure blood pressure over a long period of time.

Furthermore, recent study results have shown that home blood pressure, which is blood pressure measured at home, is more effective in the prevention, diagnosis, treatment, and so on of cardiovascular-related conditions than blood pressure measured at a hospital or during a health examination (casual blood pressure). Accordingly, sphygmomanometers for home use have become widely prevalent, and home blood pressure values have started to become used in diagnoses.

In order to improve the measurement precision of sphygmomanometers, JP H7-51233A (called "Patent Literature 1" hereinafter) discloses an invention in which processing for correcting error in a measurement value that is dependent on the characteristics of the pressure sensor for blood pressure measurement is performed in the production stage of the electronic sphygmomanometer.

JP H2-19133A (called "Patent Literature 2" hereinafter) and U.S. Pat. No. 7,594,892 (called "Patent Literature 3" hereinafter) disclose techniques for improving the reliability of blood pressure measurement values using two pressure sensors.

According to the electronic sphygmomanometer disclosed in Patent Literature 1,the correction regarding the pressure sensor is performed based on differences in the characteristics of the individuals electronic sphygmomanometers in the electronic sphygmomanometer production stage; however, unlike a sphygmomanometer used in a medical facility such as a hospital, a sphygmomanometer for home use is generally not periodically corrected after purchase, except for in certain situations such as a malfunction.

For example, even if the pressure sensor output, which is of utmost importance in blood pressure measurement, deviates beyond a specified tolerance margin, there is no way to know that this has happened, and therefore, it is not clear whether blood pressure measurement values are correct. For this reason, even if there is a large difference between a blood pressure measurement value and the normal blood pressure measurement value or the casual blood pressure measurement value, it is not clear whether the blood pressure values are actually different, or the blood pressure values are different due to error in the pressure sensor of the sphygmomanometer, thus causing concern on the part of the user.

Meanwhile, some sphygmomanometers for medical facilities include two pressure sensors, and pressure is monitored based on the output of these pressure sensors. However, the functions of these two pressure sensors are used for different purposes in such sphygmomanometers. That is, the blood pressure is calculated using cuff pressure information obtained by one of the pressure sensors, and abnormality detection is performed based on the output of the other pressure sensor.

Specifically, an abnormality is detected if the pressure value detected by the pressure sensor greatly exceeds 300 mmHg, for example. In this case, safety is ensured by stopping the pump and releasing the valve. Accordingly, the other pressure sensor is applied as a safety measure specified in the Japanese medical standard IEC 60601-2-30, and does not guarantee the precision of the one pressure sensor used for blood pressure measurement.

In light of this, it is necessary for the precision of the one pressure sensor, which is used for detecting blood pressures, to be guaranteed by that pressure sensor itself. There is thus a demand for a high-precision pressure sensor that is not influenced by external disturbances such as temperature changes, that changes little over time, and that is inexpensive. Furthermore, providing two pressure sensors that perform different functions means that the malfunction rate of the sphygmomanometer due to malfunctions in the pressure sensors will simply be double the malfunction rate of a sphygmomanometer that has only one pressure sensor.

Meanwhile, a pressure sensor used in an electronic sphygmomanometer measures pressures of fluids, liquids, and so on using a pressure-sensitive element via a diaphragm (a stainless steel diaphragm, a silicon diaphragm, or the like), converts the measurement into an electric signal, and outputs the signal.

For example, in the case of a diffused piezoresistive semiconductor pressure sensor, a semiconductor strain gauge is provided on the surface of the diaphragm, and a change in electrical resistance caused by a piezoresistance effect occurring when the diaphragm deforms due to an outside force (a pressure) is converted into an electric signal.

Meanwhile, with an electrostatic capacitance pressure sensor, a capacitor is formed by opposing a glass fixed electrode and a silicon mobile electrode, and a change in electrostatic capacitance produced when the mobile electrode deforms due to an outside force (a pressure) is converted into an electric signal.

The reliability of blood pressure measurement values is maintained because only an outside force (a pressure) that is to be measured is applied to the pressure sensor. However, because the amount of deformation in the diaphragm, the amount of deformation in the mobile electrode, and so on are on the order of microns, such pressure sensors are extremely susceptible to extraneous outside stress, and it is therefore necessary to carefully consider the peripheral structure of the pressure sensor. Specific peripheral structures for a pressure sensor, however, are neither disclosed nor considered in Patent Literature 1 through 3 below.

Patent Literature 1: JP-H7-51233A
Patent Literature 2: JP-H2-19133A
Patent Literature 3: U.S. Pat. No. 7,594,892

SUMMARY OF INVENTION

Therefore one or more embodiments of the present invention provide an electronic sphygmomanometer that includes, as a structure in which a pressure sensor used in the electronic sphygmomanometer is disposed, a peripheral structure for the pressure sensor that can improve the reliability of blood pressure measurement values.

An electronic sphygmomanometer according to one or more embodiments of the present invention includes: a cuff that is worn on a measurement area; an inflation and deflation unit that adjusts a pressure applied to the cuff; a pressure detecting unit, including a first pressure sensor and a second pressure sensor, for detecting a cuff pressure within the cuff based on pressure information outputted from the first pressure sensor and the second pressure sensor; and a blood pressure calculation unit that calculates a blood pressure based on a change in the cuff pressure detected by the pressure detecting unit.

According to one or more embodiments of the present invention, the first pressure sensor and the second pressure sensor are disposed upon a first main surface of an internal circuit board; the first pressure sensor has a first air port that protrudes on a second main surface that is on the opposite side of the internal circuit board as the first main surface; the second pressure sensor has a second air port that protrudes on the second main surface of the internal circuit board; a pressure sensor air tube that allows the first air port and the second air port to communicate with each other is connected to the first air port and the second air port; a branching air tube that branches from a cuff air tube connected to the cuff is connected to the pressure sensor air tube.

According to one or more embodiments of the present invention, the pressure sensor air tube includes: a first air port connection head connected to the first air port; a second air port connection head connected to the second air port; a first connection tube provided in the first air port connection head and to which the branching air tube is connected; and a second connection tube that connects the first air port connection head and the second air port connection head.

According to one or more embodiments of the present invention, the second connection tube has a stress reduction function that reduces stress arising in the second connection tube itself when the first air port connection head and the second air port connection head are mounted to the first air port and the second air port respectively.

In the electronic sphygmomanometer according to one or more embodiments of the present invention, as the stress reduction function, the thickness of the second connection tube is lower than the thickness of the first connection tube.

In the electronic sphygmomanometer according to one or more embodiments of the present invention, as the stress reduction function, a tube having a bulging structure is used as the second connection tube.

In the electronic sphygmomanometer according to one or more embodiments of the present invention, as the stress reduction function, a tube having an accordion structure is used as the second connection tube.

In the electronic sphygmomanometer according to one or more embodiments of the present invention, as the stress reduction function, a different member that is more flexible than the first connection tube is used as the second connection tube.

In the electronic sphygmomanometer according to one or more embodiments of the present invention, it is possible to provide an electronic sphygmomanometer including a structure for disposing a pressure sensor that can improve the reliability of blood pressure measurement values.

DETAILED DESCRIPTION OF INVENTION

Figure 1:
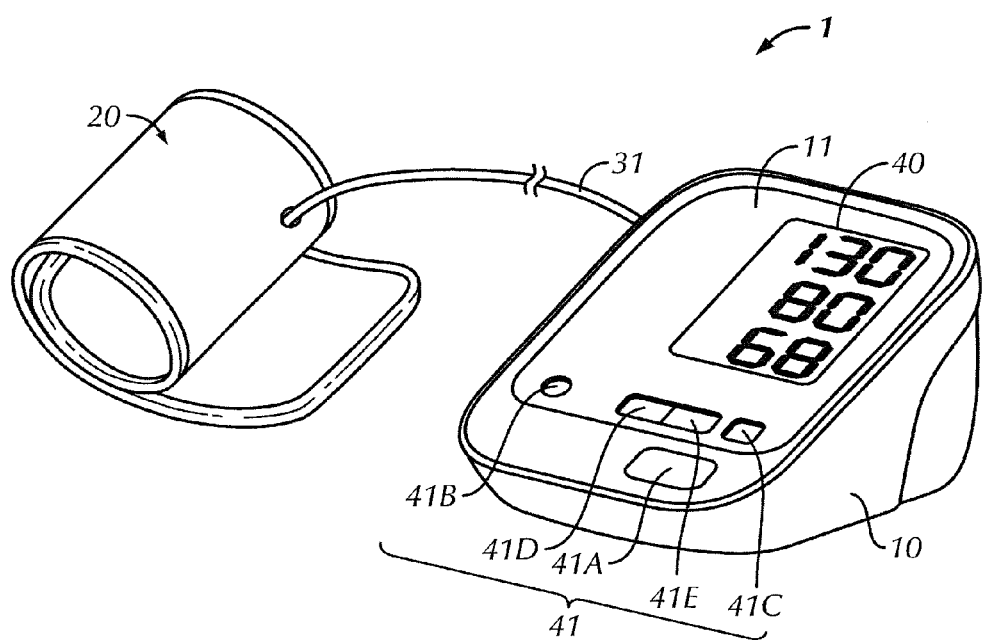
FIG. 1 is a perspective view of the outside of an electronic sphygmomanometer according to an embodiment.

Hereinafter, an electronic sphygmomanometer according to one or more embodiments of this invention will be described with reference to the drawings. When numbers, amounts, and so on are discussed in the following embodiments, it should be noted that unless explicitly mentioned otherwise, the scope of the present invention is not necessarily limited to those numbers, amounts, and so on. Furthermore, in the case where multiple embodiments are given hereinafter, it is assumed from the outset that the configurations of the respective embodiments can be combined as appropriate unless explicitly mentioned otherwise. In the drawings, identical reference numerals refer to identical or corresponding elements; there are also cases where redundant descriptions are omitted.

The present embodiment describes an electronic sphygmomanometer that calculates blood pressures through an oscillometric method using the upper arm as a measurement area, and as an example, includes two pressure sensors. Note that the method applied for the blood pressure calculation is not limited to an oscillometric method.

External View of Electronic Sphygmomanometer 1

Figure 2:
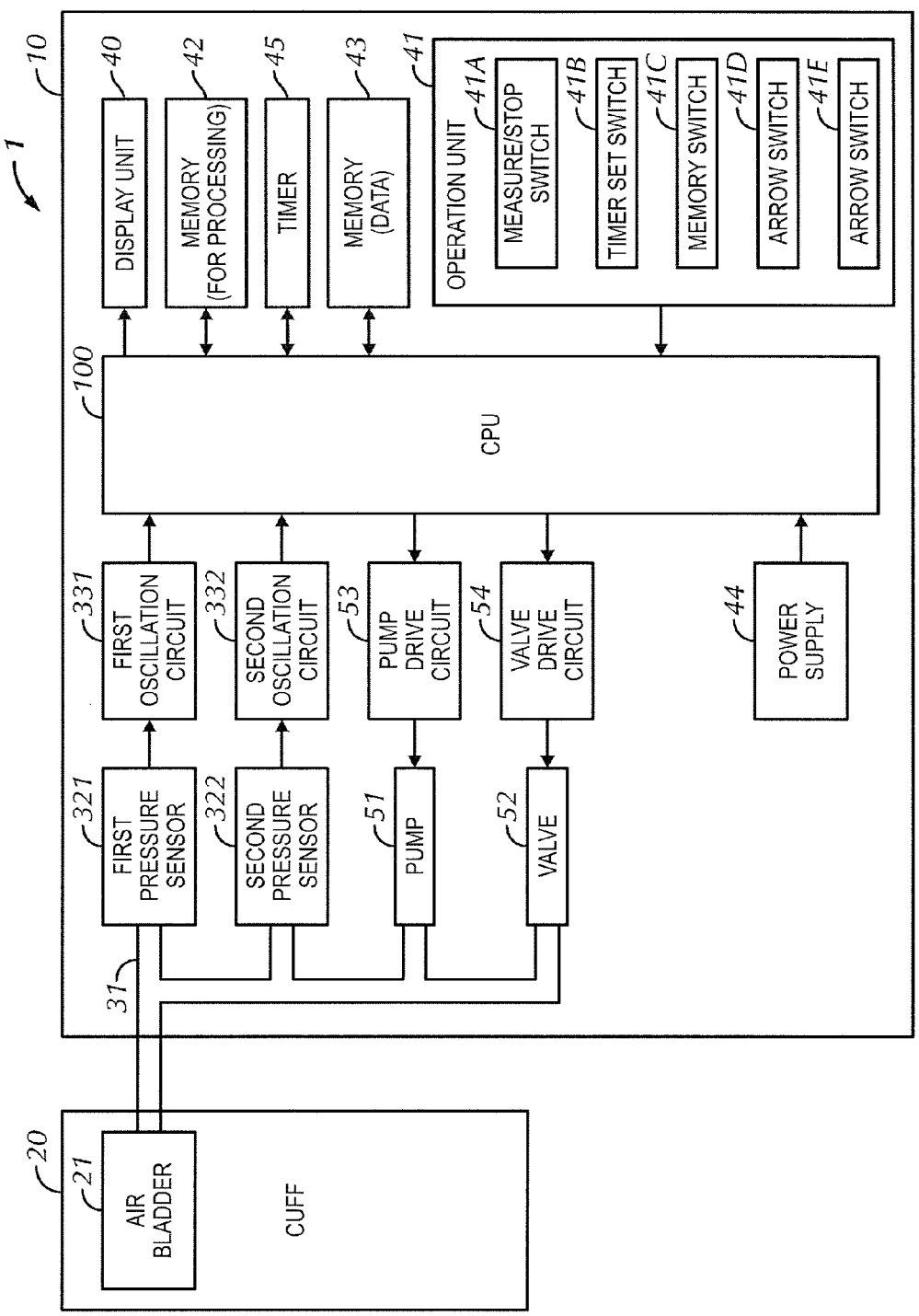
FIG. 2 is a diagram illustrating a hardware configuration of the electronic sphygmomanometer according to the embodiment.

FIG. 1 is a diagram illustrating an external view of an electronic sphygmomanometer 1 according to an embodiment of this invention. FIG. 2 is a block diagram illustrating the hardware configuration of the electronic sphygmomanometer according to the embodiment of the present invention. As seen in FIGS. 1 and 2, the electronic sphygmomanometer 1 includes a main body portion 10, a front cover 11, and a cuff 20 that can be wrapped around the upper arm of a measurement subject. The cuff 20 includes an air bladder 21. A display unit 40 configured of a liquid-crystal display or the like and an operation unit 41 configured of multiple switches for accepting instructions from a user (measurement subject) are disposed on the front cover 11.

In addition to the aforementioned display unit 40 and operation unit 41, the main body portion 10 includes: a CPU (central processing unit) 100 for carrying out centralized control of the respective elements and performing various types of computational processes; a processing memory 42 that stores programs, data, and so on for causing the CPU 100 to perform predetermined tasks; a data storage memory 43 for storing measured blood pressure data and so on; a power supply 44 for supplying power to the various elements of the main body portion 10; and a timer 45 that measures the current time and outputs the measured time data to the CPU 100.

The operation unit 41 includes: a measure/stop switch 41A that accepts the input of an instruction for turning the power on or off and accepts an instruction for starting and stopping measurement; a timer set switch 41B manipulated in order to set the timer 45; a memory switch 41C for accepting an instruction to read out information stored in the memory 43, such as blood pressure data, from the memory 43 and display that information in the display unit 40; and arrow switches 41D and 41E for accepting instructions to raise/lower numbers when setting the timer and memory numbers when calling information from a memory.

The main body portion 10 further includes a cuff pressure adjustment mechanism having a pump 51 and an exhaust valve (called simply a "valve" hereinafter) 52. An air system configured of the pump 51, the valve 52, and a first pressure sensor 321 and second pressure sensor 322 for detecting pressures within the air bladder 21 (cuff pressures) is connected, via a cuff air tube 31, to the air bladder 21 enclosed within the cuff 20.

The main body portion 10 further includes the aforementioned air system, the cuff pressure adjustment mechanism, and a first oscillation circuit 331 and second oscillation circuit 332. The cuff pressure adjustment mechanism includes a pump drive circuit 53 and a valve drive circuit 54, in addition to the pump 51 and the valve 52.

The pump 51 supplies air to the air bladder 21 in order to increase the cuff pressure. The valve 52 is opened/closed in order to discharge or inject air into the air bladder 21. The pump drive circuit 53 controls the driving of the pump 51 based on a control signal supplied from the CPU 100. The valve drive circuit 54 controls the opening/closing of the valve 52 based on a control signal supplied from the CPU 100.

Electrostatic capacitance pressure sensors, for example, are used for the first pressure sensor 321 and the second pressure sensor 322. With an electrostatic capacitance pressure sensor, a capacity value changes in accordance with a detected cuff pressure. The first oscillation circuit 331 and the second oscillation circuit 332 are respectively connected to corresponding pressure sensors, and oscillate based on the capacity values of the corresponding pressure sensors.

As a result, signals having frequencies based on the capacity values of the corresponding pressure sensors (called "frequency signals" hereinafter) are outputted. The outputted frequency signals are supplied to the CPU 100. The CPU 100 detects a pressure by converting the frequency signal inputted from the first oscillation circuit 331 or the second oscillation circuit 332 into a pressure.

Figure 3:
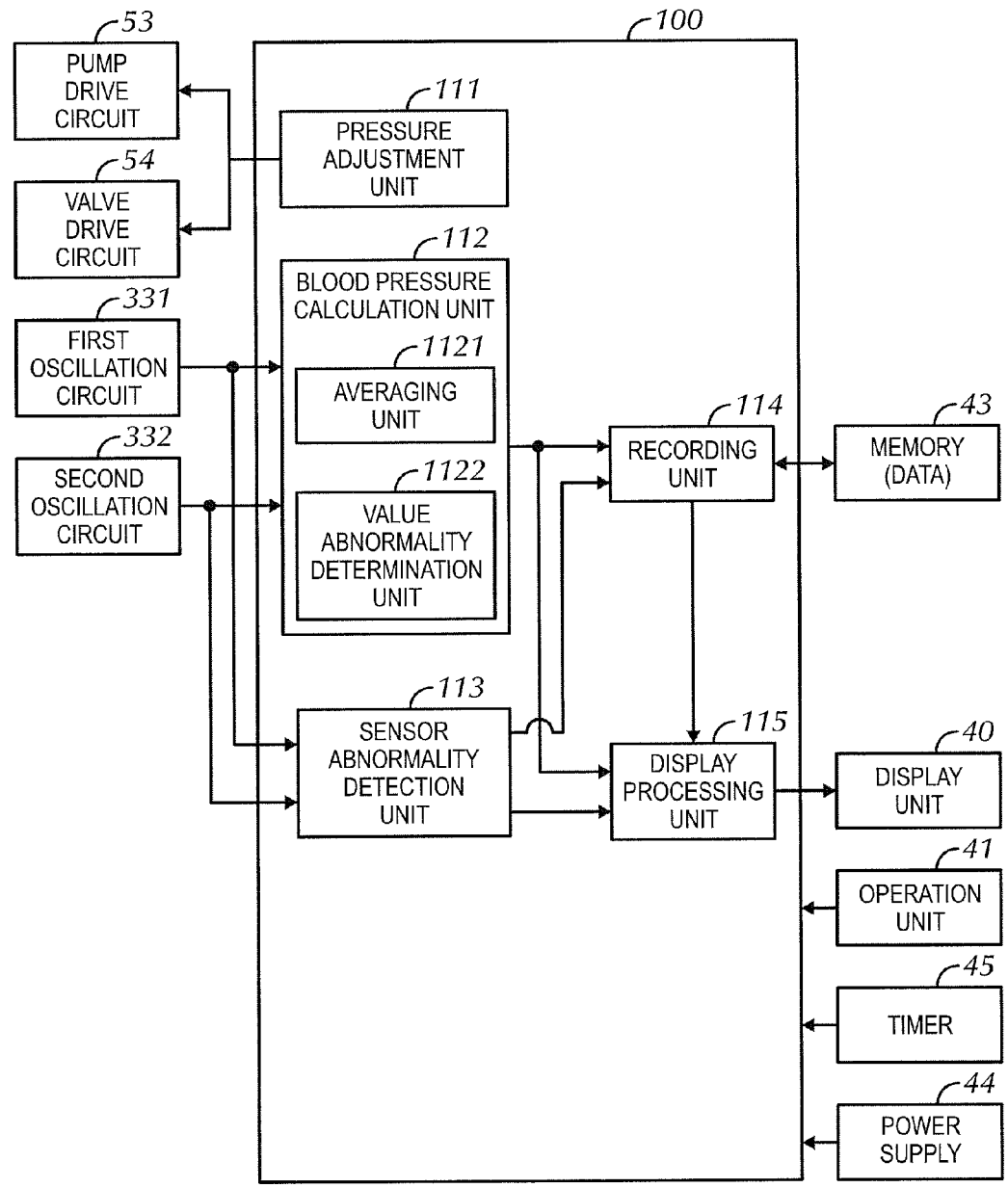
FIG. 3 is a diagram illustrating a functional configuration of the electronic sphygmomanometer according to the embodiment.

FIG. 3 illustrates the functional configuration of the electronic sphygmomanometer 1 according to the present embodiment. As shown in FIG. 3, the CPU 100 includes a pressure adjustment unit 111, a blood pressure calculation unit 112, a sensor abnormality detection unit 113, a recording unit 114, and a display processing unit 115.

The pressure adjustment unit 111 adjusts the cuff pressure by controlling the pump 51 and the valve 52 via the pump drive circuit 53 and the valve drive circuit 54 in order to inject/discharge air into/from the air bladder 21 via the cuff air tube 31.

According to one or more embodiments of the present invention, the blood pressure calculation unit 112 includes an averaging unit 1121 and a value abnormality determination unit 1122. The blood pressure calculation unit 112 detects pulse wave amplitude information based on the frequency signal inputted from the first oscillation circuit 331 or the second oscillation circuit 332 (this frequency signal refers to a pressure information signal), calculates a systolic blood pressure and a diastolic blood pressure based on the detected pulse wave amplitude information through the oscillometric method, and also calculates the number of pulse beats per predetermined amount of time based on the detected pulse wave amplitude information.

Specifically, as the cuff pressure is gradually increased (or decreased) to a predetermined value by the pressure adjustment unit 111, the pulse wave amplitude information is detected based on the cuff pressure inputted from the first oscillation circuit 331 or the second oscillation circuit 332, and the systolic blood pressure and the diastolic blood pressure of the measurement subject are calculated based on the detected pulse wave amplitude information. A known conventional method can be applied in the calculation of the blood pressure and the calculation of the pulse by the blood pressure calculation unit 112 through the oscillometric method.

The sensor abnormality detection unit 113 takes the frequency signals outputted from the first oscillation circuit 331 and the second oscillation circuit 332 as inputs, and detects abnormalities in the first pressure sensor 321 and the second pressure sensor 322 by analyzing the inputted signals.

The recording unit 114 has functionality for reading out data from the memory 43 or writing data into the memory 43. Specifically, the recording unit 114 inputs data outputted from the blood pressure calculation unit 112, and stores the inputted data (blood pressure measurement data) in a predetermined storage region of the memory 43. Furthermore, the recording unit 114 takes the data outputted from the sensor abnormality detection unit 113 as an input, and stores the inputted data (that is, the result of detecting abnormalities in the pressure sensors) in a predetermined storage region of the memory 43. In addition, the recording unit 114 reads out measurement data from a predetermined storage region of the memory 43 based on an operation made through the memory switch 41C of the operation unit 41, and outputs the measurement data to the display processing unit 115.

The display processing unit 115 inputs supplied data, converts the data into a displayable format, and displays the converted data in the display unit 40.

FIG. 3 illustrates only the circuits around the CPU 100 that directly input/output to/from the CPU 100.

Figure 4:
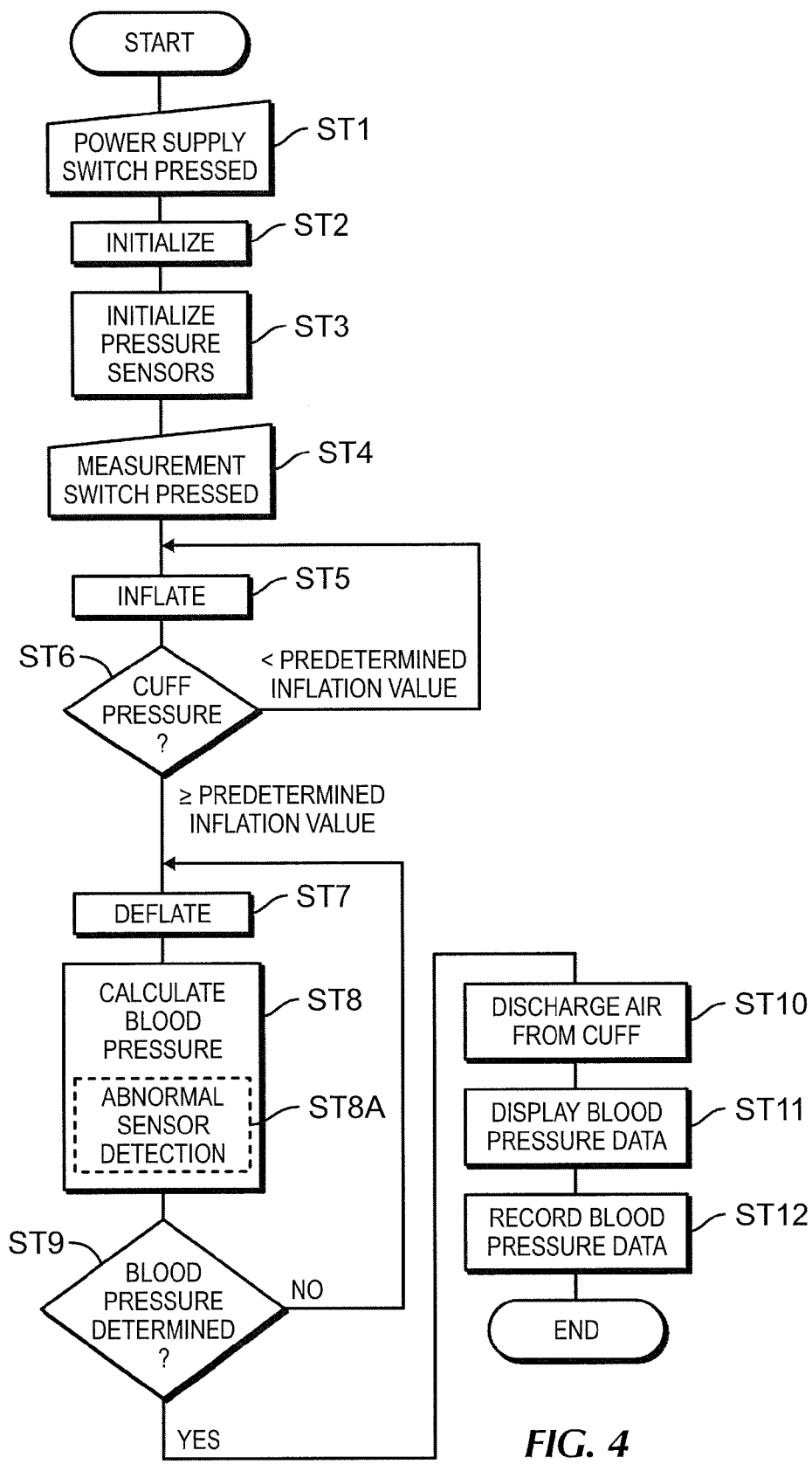
FIG. 4 is a flowchart illustrating a blood pressure measurement process according to the embodiment.

FIG. 4 illustrates a procedure carried out in a blood pressure measurement process according to the present embodiment. The flowchart in FIG. 4 illustrating the stated procedure is stored in advance in a memory 42 as a program, and the blood pressure measurement process illustrated in FIG. 4 is realized by the CPU 100 reading out the program from the memory 42 and executing instructions.

First, when the measurement subject manipulates (presses) the measure/stop switch 41A (step ST1), the CPU 100 resets a working memory (not shown) (ST2).

Next, the first pressure sensor 321 and the second pressure sensor 322 are adjusted to 0 mmHg (ST3).

Here, the measurement subject wraps the cuff 20 around the measurement area (the upper arm) of the measurement subject and wears the cuff 20. When the measurement subject operates (presses) the measure/stop switch 41A after wrapping the cuff 20 around the measurement area (step ST4), the pressure adjustment unit 111 outputs control signals to the pump drive circuit 53 and the valve drive circuit 54. Based on the control signals, the valve drive circuit 54 closes the valve 52, and the pump drive circuit 53 drives the pump 51. As a result, the cuff pressure is gradually increased to a predetermined pressure (steps ST5, ST6).

After the cuff 20 has been inflated to the predetermined pressure ("≧predetermined inflation value" in step ST6), the pressure adjustment unit 111 outputs control signals to the pump drive circuit 53 and the valve drive circuit 54. Based on the control signals, the pump drive circuit 53 stops the pump 51, after which the valve drive circuit 54 gradually controls the valve 52 so as to open. The cuff pressure gradually decreases as a result (step ST7).

During this pressure reduction process, the blood pressure calculation unit 112 detects the pulse wave amplitude information based on the frequency signal outputted from the first oscillation circuit 331 or the second oscillation circuit 332, or in other words, based on a cuff pressure signal detected by the first pressure sensor 321 or the second pressure sensor 322; a predetermined computation is then carried out on the detected pulse wave amplitude information. The systolic blood pressure and the diastolic blood pressure are calculated through this computation (steps ST8, ST9). The pulse wave amplitude information expresses a component of the change in volume of an artery in the measurement area, and is included in the detected cuff pressure signal. The computations during the calculation of the blood pressure by the blood pressure calculation unit 112 are carried out in accordance with the characteristics of the pressure sensors. Note that the blood pressure measurement is not limited to being carried out during the pressure reduction process, and may instead be carried out during the process of increasing the pressure (step ST5).

When the systolic blood pressure and diastolic blood pressure have been calculated and determined (YES in step ST9), the pressure adjustment unit 111 fully opens the valve 52 via the valve drive circuit 54, and quickly discharges the air within the cuff 20 (step ST10).

The blood pressure data calculated by the blood pressure calculation unit 112 is outputted to the display processing unit 115 and the recording unit 114. The display processing unit 115 takes the blood pressure data as its input, and displays that data in the display unit 40 (step ST11). Meanwhile, the recording unit 114 takes the blood pressure data as its input, and stores that data in a predetermined storage region of the memory 43 in association with time data inputted from the timer 45 (step ST12).

Note that the blood pressure calculation unit 112 can also calculate the number of pulse beats based on the detected pulse wave amplitude information. The calculated number of pulse beats is displayed in the display unit 40 by the display processing unit 115, and is stored in the memory 43 in association with the blood pressure data by the recording unit 114.

Note that the operations described thus far are the same as those performed by conventional sphygmomanometers. With conventional electronic sphygmomanometers, users have been unable to determine whether the pressure sensors, which are of utmost importance when calculating blood pressures, are operating normally or have malfunctioned. Thus, for example, in the case where a blood pressure measurement value differs greatly (for example, a difference of more than 10 mmHg) from a normal value (for example, a measurement value obtained the previous day, a measurement value obtained at a hospital, or the like), it is not known whether that value comes from actual biological information of the measurement subject or if the pressure sensor has merely malfunctioned, which has caused concern on the part of the user.

Accordingly, the electronic sphygmomanometer 1 according to the present embodiment includes the first pressure sensor 321 and the second pressure sensor 322, and calculates blood pressures by taking the average value of the cuff pressures detected by these pressure sensors. As a result, even in the case where fluctuations have occurred in the detection accuracy of one of the pressure sensors due to changes over time, the reliability of blood pressure measurement values can be improved by calculating the average value.

Structure in which Pressure Sensors are Disposed

Figure 5:
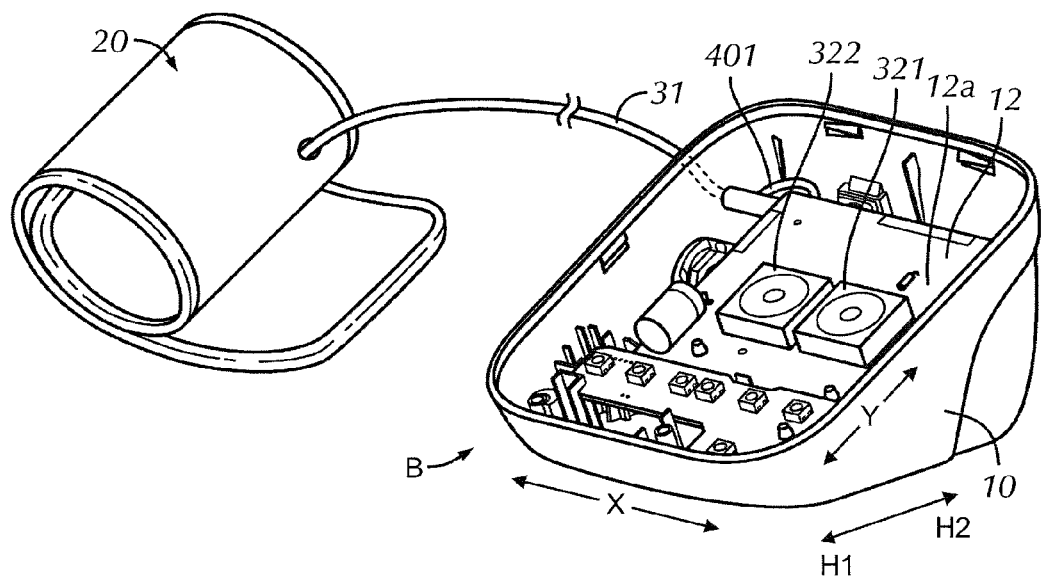
FIG. 5 is a perspective view illustrating the internal structure of the electronic sphygmomanometer according to the embodiment, where a front cover has been removed.

Next, a structure for disposing the first pressure sensor 321 and the second pressure sensor 322 will be described with reference to FIGS. 5 through 7. FIG. 5 is a perspective view illustrating the internal structure of the electronic sphygmomanometer 1 according to the present embodiment, where the front cover 11 has been removed from the main body portion 10. The electronic sphygmomanometer 1 according to present embodiment has a structure in which, when the electronic sphygmomanometer 1 is placed on a mount surface B, the front cover 11 is sloped.

In order to make it easier for the user (measurement subject) to view the display unit 40 and to make it easier to operate the operation unit 41 provided in the front cover 11, the front cover 11 is sloped (the Y direction shown in FIG. 5) so that the side facing the user (measurement subject) (the front side; the side indicated as H1 in FIG. 5) is lower and the rear side (the side indicated as H2 in FIG. 5) is higher. For this reason, an internal circuit board 12 housed internally is also disposed parallel to the front cover 11, and is thus sloped so that the front side (the side indicated as H1 in FIG. 5) is lower and the rear side (the side indicated as H2 in FIG. 5) is higher.

As shown in FIG. 5, the first pressure sensor 321 and the second pressure sensor 322 are disposed on a front surface side 12a of the internal circuit board 12, which corresponds to a first main surface, along the horizontal direction (the X direction in FIG. 5) that is orthogonal to the direction in which the front cover 11 of the electronic sphygmomanometer 1 slopes. In the present embodiment, for example, the first pressure sensor 321 and the second pressure sensor 322 are disposed along a direction orthogonal to the direction in which the front cover 11 of the electronic sphygmomanometer 1 slopes. FIGS. 6 and 7 are diagrams viewing the internal circuit board 12 from a rear surface side, serving as a second main surface that is on the opposite side as the first main surface. In addition, FIG. 6 illustrates a state in which a pressure sensor air tube 500 is not attached to the first pressure sensor 321 and the second pressure sensor 322, whereas FIG. 7 illustrates a state in which the pressure sensor air tube 500 is attached to the first pressure sensor 321 and the second pressure sensor 322.

Figure 6:
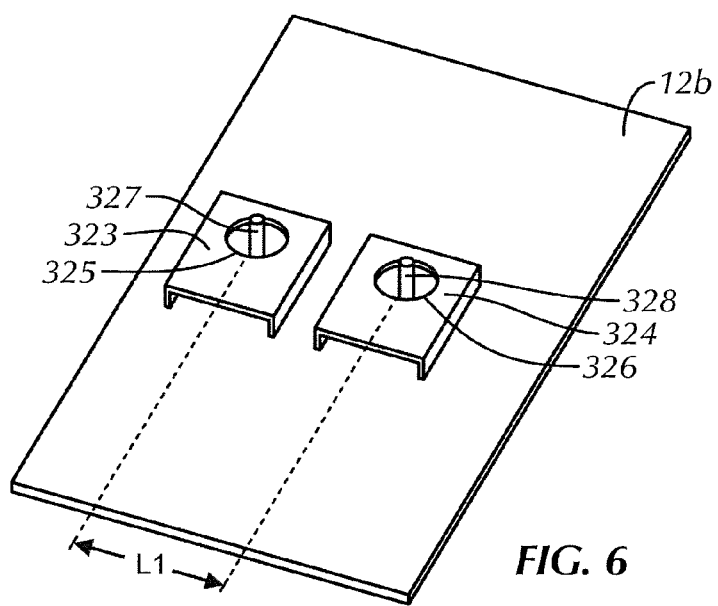
FIG. 6 is a first diagram illustrating a structure in which an internal circuit board and two pressure sensors used in the electronic sphygmomanometer according to the embodiment are viewed from the rear side of the internal circuit board.

As shown in FIG. 6, a first air port 327 of the first pressure sensor 321 and a second air port 328 of the second pressure sensor 322 are disposed, at a predetermined distance (L1) from each other, on the rear surface side of the internal circuit board 12 so as to protrude. In addition, the first oscillation circuit is formed on a rear surface 12b of the internal circuit board 12 in a position in the periphery of the first air port 327, and a first shielding plate 323 for protecting the first oscillation circuit is attached upon the rear surface 12b of the internal circuit board 12. A first opening 325 for exposing the first air port 327 is provided in the first shielding plate 323. A predetermined gap is formed between the first shielding plate 323 and the rear surface of the internal circuit board 12.

Likewise, the second oscillation circuit is formed on the rear surface 12b of the internal circuit board 12 in a position in the periphery of the second air port 328, and a second shielding plate 324 for protecting the second oscillation circuit is attached upon the rear surface 12b of the internal circuit board 12. A second opening 326 for exposing the second air port 328 is provided in the second shielding plate 324. A predetermined gap is formed between the second shielding plate 324 and the rear surface of the internal circuit board 12.

Figure 7:
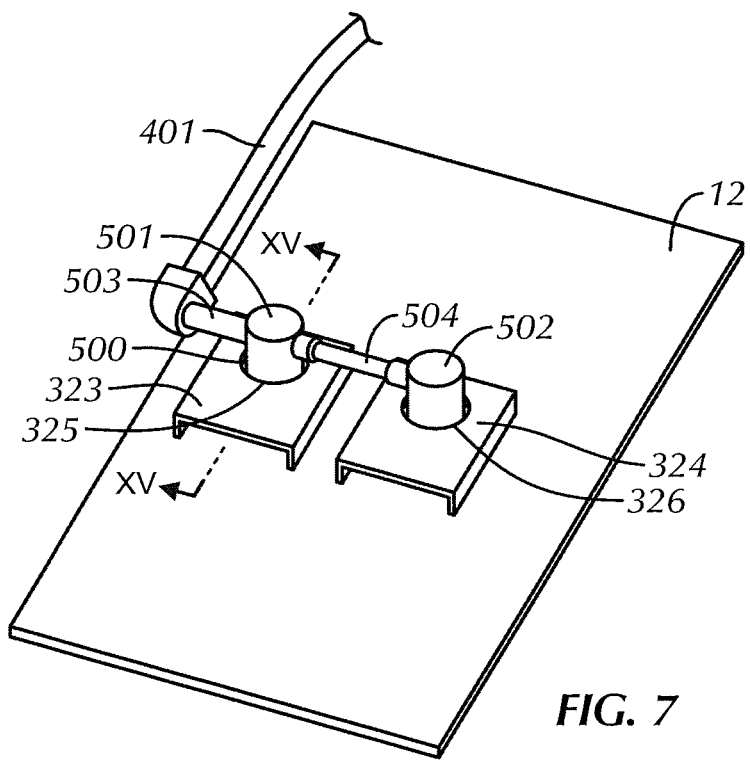
FIG. 7 is a second diagram illustrating a structure in which an internal circuit board and two pressure sensors used in the electronic sphygmomanometer according to the embodiment are viewed from the rear side of the internal circuit board.

As shown in FIG. 7, during actual use, the pressure sensor air tube 500 is attached to the first air port 327 of the first pressure sensor 321 and the second air port 328 of the second pressure sensor 322. A branching air tube 401 that branches from the cuff air tube 31 is connected to the pressure sensor air tube 500.

The pressure sensor air tube 500 includes: a first air port connection head 501 that is connected to the first air port 327; a second air port connection head 502 that is connected to the second air port 328; a first connection tube 503 that is provided in the first air port connection head 501 and that is connected to the branching air tube 401; and a second connection tube 504 that connects the first air port connection head 501 and the second air port connection head 502. An elastomer (rubber, a thermoplastic elastomer) or the like is used as the material for the pressure sensor air tube 500.

According to the structure in which the pressure sensors are disposed in the present embodiment, stress resulting when the load of the pressure sensor air tube 500 is applied to the pressure sensors can be distributed approximately uniformly between the first pressure sensor 321 and the second pressure sensor 322. For example, in the case where the two pressure sensors are arranged and disposed in the vertical direction (the direction orthogonal to the X direction in FIG. 5), the load from the pressure sensor air tube 500 is applied to the first pressure sensor 321 and the second pressure sensor 322 in a non-uniform manner due to the slope of the internal circuit board 12.

However, in the present embodiment, the first pressure sensor 321 and the second pressure sensor 322 are disposed, on the front surface side 12a that serves as the first main surface of the internal circuit board 12, following the horizontal direction (the X direction FIG. 5) that is orthogonal to the direction in which the internal circuit board 12 slopes; as a result, the first pressure sensor 321 and the second pressure sensor 322 are disposed having the same height position from the mount surface B.

Accordingly, as shown in FIG. 7, when the pressure sensor air tube 500 is attached to the first pressure sensor 321 and the second pressure sensor 322, the load of the pressure sensor air tube 500 is distributed approximately uniformly between the first pressure sensor 321 and the second pressure sensor 322, which makes it possible to make the stress applied to the pressure sensors approximately equal.

Figure 8:
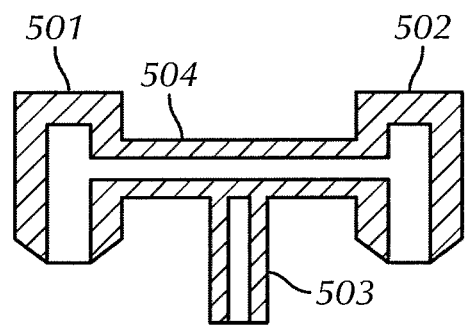
FIG. 8 is a cross-sectional view illustrating the structure of an air tube used in the electronic sphygmomanometer according to the embodiment.

As a result, it is possible to improve the reliability of blood pressure measurement values obtained by an electronic sphygmomanometer that uses two pressure sensors, or the first pressure sensor 321 and the second pressure sensor 322. Note that in order to distribute the load of the pressure sensor air tube 500 more equally between the first pressure sensor 321 and the second pressure sensor 322, according to one or more embodiments of the present invention, as shown in FIG. 8, the first connection tube 503 to which the branching air tube 401 is connected is disposed in a position that is centered on the first air port connection head 501 and the second air port connection head 502.

Details of Structure of Pressure Sensor Air Tube 500

Next, details of the structure of the pressure sensor air tube will be described with reference to FIGS. 9 through 14. First, details of the structure of the pressure sensor air tube 500 illustrated in FIG. 7 will be described with reference to FIGS. 9 and 10.

As described above, the pressure sensor air tube 500 includes: the first air port connection head 501 that is connected to the first air port 327; the second air port connection head 502 that is connected to the second air port 328; the first connection tube 503 that is provided in the first air port connection head 501 and that is connected to the branching air tube 401; and the second connection tube 504 that connects the first air port connection head 501 and the second air port connection head 502. An elastomer (rubber, a thermoplastic elastomer) or the like is used as the material for the pressure sensor air tube 500.

The outer diameter of the first connection tube 503 is represented by Db, whereas the inner diameter is represented by Dc. As a specific example of the dimensions, the outer diameter (Db) is approximately 4.5 mm, whereas the inner diameter (Dc) is approximately 2 mm Meanwhile, the outer diameter of the second connection tube 504 is represented by Da, whereas the inner diameter is represented by Dc, which is the same as with the first connection tube 503. As a specific example of the dimension, the outer diameter (Da) is approximately 4 mm.

In this manner, the thickness of the second connection tube 504 is set to be lower than the thickness of the first connection tube 503, and thus the second connection tube 504 is more flexible than the first connection tube 503. As a result, even if error has occurred in the structural dimensions of the pressure sensor air tube 500, that is, in the distance between the first air port 327 and the second air port 328 (L1; see FIG. 6), the second connection tube 504 can extend/contract, which makes it possible to absorb the error in the structural dimensions of the pressure sensor air tube 500.

Accordingly, in the case where the pressure sensor air tube 500 has been attached to the first pressure sensor 321 and the second pressure sensor 322, the second connection tube 504 provides a stress reduction function (Sf), which makes it possible to reduce unnecessary stress (compression stress/pulling stress) from being applied to the first pressure sensor 321 and the second pressure sensor 322. As a result, it is possible to improve the reliability of blood pressure measurement values obtained by an electronic sphygmomanometer that uses two pressure sensors, or the first pressure sensor 321 and the second pressure sensor 322.

Details of Structures of Pressure Sensor Air Tube 500A/500B

Figure 11:
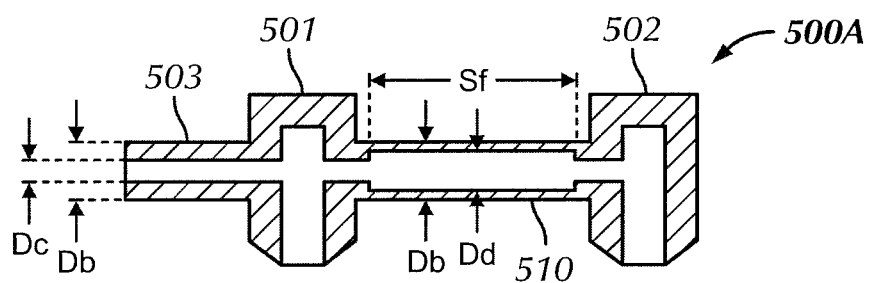
FIG. 11 is a cross-sectional view corresponding to the X-X line in FIG. 9, illustrating another structure of an air tube used in the electronic sphygmomanometer according to the embodiment.
Figure 12:
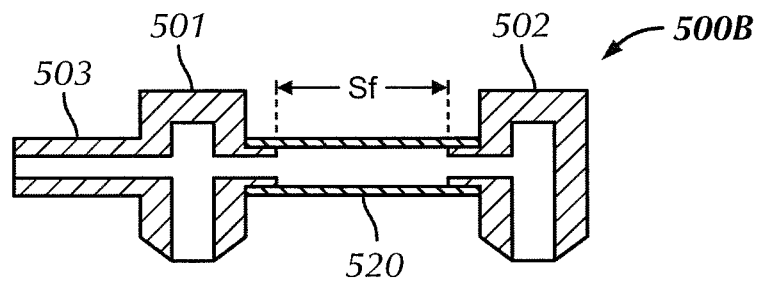
FIG. 12 is a cross-sectional view corresponding to the X-X line in FIG. 9, illustrating yet another structure of an air tube used in the electronic sphygmomanometer according to the embodiment.

Next, details of the structure of a pressure sensor air tube 500A serving as a variation will be described with reference to FIG. 11. FIG. 11 is a cross-sectional view corresponding to the X-X line in FIG. 9. In the pressure sensor air tube 500A, the outer diameter of the first connection tube 503 and the outer diameter of a second connection tube 510 have the same outer diameter dimension (Db), but the inner diameter dimension (Dd) of the second connection tube 510 is set to be greater than the inner diameter dimension (Dc) of the first connection tube 503. As a specific example of the dimension, the inner diameter dimension (Dd) of the second connection tube 510 is approximately 2.5 mm.

Employing this configuration also makes the thickness of the second connection tube 510 lower than the thickness of the first connection tube 503, which makes it possible to provide a similar stress reduction function (Sf) as the pressure sensor air tube 500. Note that with a pressure sensor air tube 500B shown in FIG. 12, a second connection tube 520 is, unlike the second connection tube 510 illustrated in FIG. 11, configured of a different member that is more flexible than the first connection tube 503, the first air port connection head 501, and the second air port connection head 502; however, the dimensional relationships are the same as with the second connection tube 510.

Details of Structure of Pressure Sensor Air Tube 500C

Figure 13:
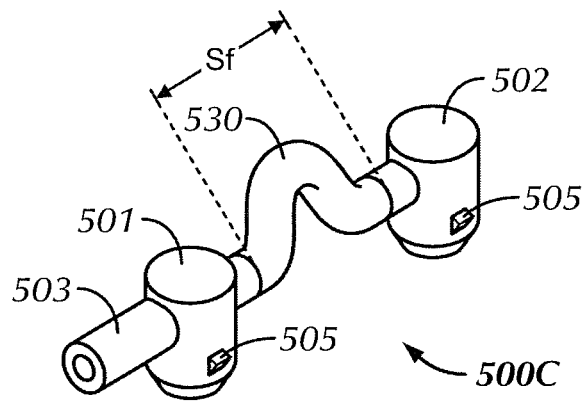
FIG. 13 is a perspective view illustrating another structure of the air tube used in the electronic sphygmomanometer according to the embodiment.

Next, details of the structure of a pressure sensor air tube 500C serving as a variation will be described with reference to FIG. 13. This pressure sensor air tube 500C employs a tube having a bulging structure as a second connection tube 530. By employing such a structure, the second connection tube 530 is capable of extending/contracting, which makes it possible to provide a similar stress reduction function (Sf) as the pressure sensor air tube 500.

Details of Structure of Pressure Sensor Air Tube 500D

Figure 14:
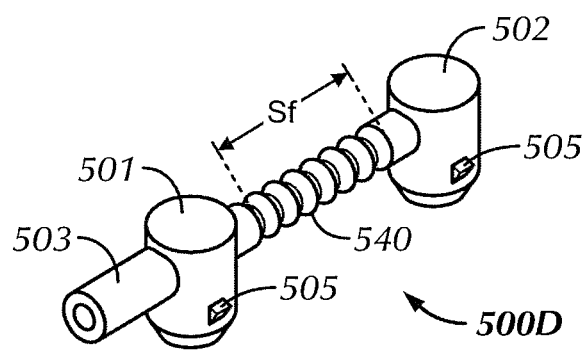
FIG. 14 is a perspective view illustrating yet another structure of the air tube used in the electronic sphygmomanometer according to the embodiment.

Next, details of the structure of a pressure sensor air tube 500D serving as a variation will be described with reference to FIG. 14. This pressure sensor air tube 500D employs a tube having an accordion structure as a second connection tube 540. By employing such a structure, the second connection tube 540 is capable of extending/contracting, which makes it possible to provide a similar stress reduction function (Sf) as the pressure sensor air tube 500.

Anchoring Structure for Pressure Sensor Air Tube 500

Next, an anchoring structure for the pressure sensor air tube 500 will be described with reference to FIG. 9 and FIGS. 15 through 17. Note that the anchoring structures for the pressure sensor air tubes 500A through 500D illustrated in FIGS. 11 through 14 are the same as the anchoring structure for the pressure sensor air tube 500. In addition, in FIG. 15, the front surface side of the internal circuit board 12 is illustrated as being on the bottom, whereas the rear surface side is illustrated as being on the top.

Figure 9:
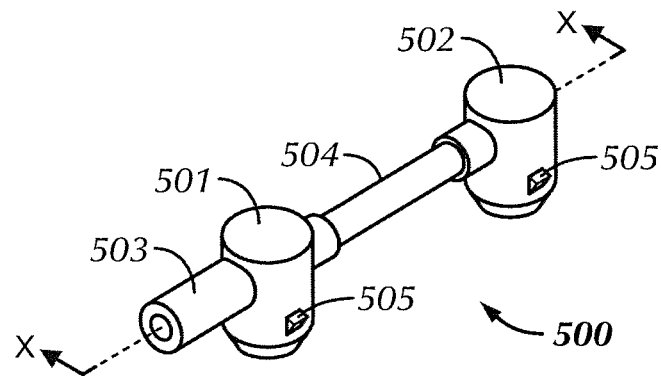
FIG. 9 is a perspective view illustrating the external appearance of the air tube used in the electronic sphygmomanometer according to the embodiment.
Figure 10:
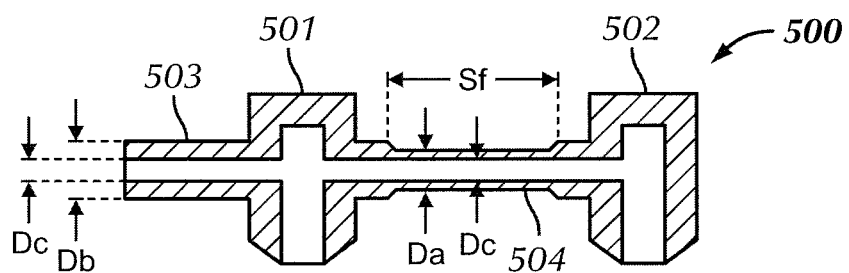
FIG. 10 is a cross-sectional view taken along the X-X line in FIG. 9.

As shown in FIG. 9, protruding members 505 that engage with the inner surface side of the first shielding plate 323 within the first opening 325 provided in the first shielding plate 323 when the first air port 327 is connected thereto are formed on the outside surface of the first air port connection head 501 in the pressure sensor air tube 500. In the present embodiment, the protruding members 505 are provided in a total of two locations that are opposite to each other by 180°.

Likewise, protruding members 505 that engage with the inner surface side of the second shielding plate 324 within the second opening 326 provided in the second shielding plate 324 when the second air port 328 is connected thereto are formed on the outside surface of the second air port connection head 502 in the pressure sensor air tube 500. In the present embodiment, the protruding members 505 are provided in a total of two locations that are opposite to each other by 180°.

Figure 15:
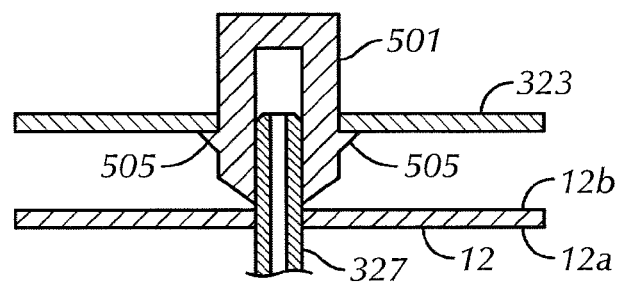
FIG. 15 is a cross-sectional view illustrating an anchoring structure for the air tube used in the electronic sphygmomanometer according to the embodiment.

As shown in FIG. 15, the same anchoring structure for the pressure sensor air tube 500 is employed for the first air port connection head 501 and the second air port connection head 502, and therefore the following will describe only the anchoring structure of the first air port connection head 501.

By inserting the first air port connection head 501 into the first air port 327 through the first opening 325 provided in the first shielding plate 323, the protruding members 505 provided on the outside surface of the first air port connection head 501 pass over the first shielding plate 323 while elastically deforming and reach a position on the inner side of the first shielding plate 323. Through this, it is possible to anchor the first air port connection head 501 to the first shielding plate 323. As a result, the first air port connection head 501 can be prevented from pulling out from the first air port 327.

Figure 16:
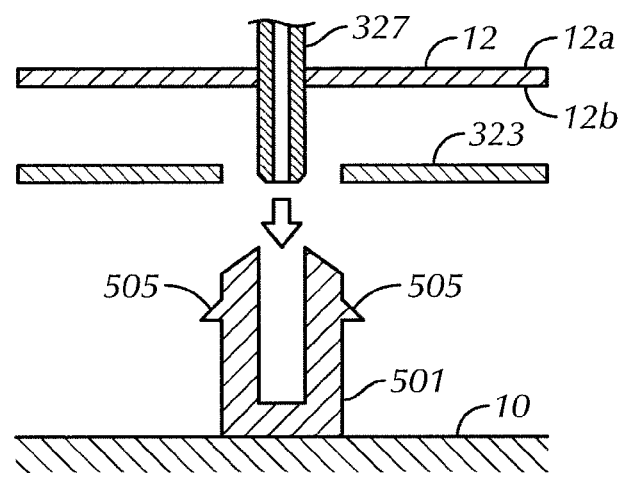
FIG. 16 is a first cross-sectional view illustrating an anchoring step for the air tube used in the electronic sphygmomanometer according to the embodiment.
Figure 17:
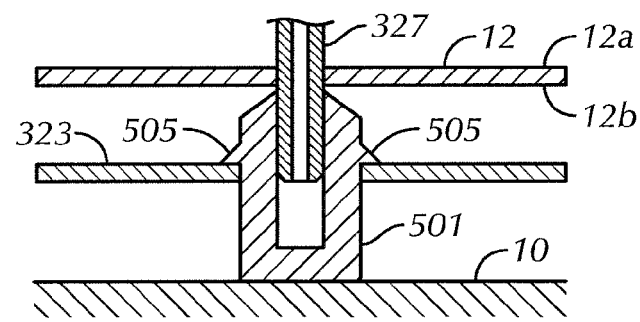
FIG. 17 is a second cross-sectional view illustrating an anchoring step for the air tube used in the electronic sphygmomanometer according to the embodiment.

Here, the anchoring of the first air port connection head 501 to the first shielding plate 323 during the assembly of the electronic sphygmomanometer 1 will be described with reference to FIGS. 16 and 17. As shown in FIG. 16, the first air port connection head 501 (pressure sensor air tube) is positioned in advance in a predetermined position on the main body portion 10.

Next, the internal circuit board 12 is positioned in a predetermined position on the main body portion 10 from above the first air port connection head 501. At this time, it is not possible for a worker to check the first air port connection head 501 visually. It can be said that because the first air port connection head 501 has an elastic force, the first air port connection head 501 can be anchored by pushing the first air port 327 into the first air port connection head 501. However, it is also thought that if the position of the first air port 327 has shifted, the internal circuit board 12 will be pushed against the main body portion 10 with the first air port connection head 501 in a bent state.

However, according to the present embodiment, the protruding members 505 are provided, and in the case where the first air port 327 has been pushed into the first air port connection head 501, the protruding members 505 pass over the first shielding plate 323 while elastically deforming and reach a position on the inner side of the first shielding plate 323; accordingly, a worker can feel the first air port 327 lock into place when the protruding members 505 return to their original forms. Through this, even though the worker cannot see that the first air port 327 has been connected to the first air port connection head 501, the worker can still confirm this connection.

Although a structure in which protruding members are provided in the air port connection heads and the protruding members engage with the shielding plates is employed in the present embodiment, embodiments of the present invention are not limited to this structure. For example, a dedicated plate for engaging with the protruding members can be provided above the internal circuit board 12. Alternatively, as a variation, a structure in which a direct engagement region is provided in the internal circuit board 12 and the air port connection heads are engaged with this engagement region can also be employed.

Furthermore, although the present embodiment describes a case where the protruding members are provided in two locations on the outside surfaces of the air port connection heads, it should be noted that in the case where priority is placed on the worker obtaining a sense of the protruding members locking into place upon returning to their original forms as described above, the configuration may be such where the protruding members are provided in only a single location on the outside surfaces of the air port connection heads.

In addition, although the present embodiment describes a case where the first air port connection head 501 and the second air port connection head 502 are provided so that the two pressure sensors can be connected to the pressure sensor air tube 500, the configuration of the present embodiment with respect to the anchoring structure for the pressure sensor air tube can be employed for a single pressure sensor as well.

Although the aforementioned embodiment describes a case where the first pressure sensor 321 and the second pressure sensor 322 are disposed on the front surface side 12a of the internal circuit board 12 and the pressure sensor air tube 500 is disposed on the rear surface side 12b of the internal circuit board 12, it should be noted that the same effects can be achieved in the case where the first pressure sensor 321 and the second pressure sensor 322 are disposed on the rear side surface 12b of the internal circuit board 12 and the pressure sensor air tube 500 is disposed on the front surface side 12a of the internal circuit board 12.

Furthermore, although the aforementioned embodiment describes a case where two pressure sensors are used, the configuration according to the embodiment can also be employed in the case where three or more pressure sensors are used.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

REFERENCE NUMERALS LIST 1 electronic sphygmomanometer
10 main body portion
11 front cover
12 internal circuit board
12a front surface side
20 cuff
21 air bladder
31 cuff air tube
40 display unit
41 operation unit
41A measure/stop switch
41B timer set switch
41C memory switch
41D, 41E arrow switch
42, 43 memory
44 power supply
45 timer
51 pump
52 valve
53 pump drive circuit
54 valve drive circuit
100 CPU (Central Processing Unit)
111 pressure adjustment unit
112 blood pressure calculation unit
1121 averaging unit
1122 value abnormality determination unit
113 sensor abnormality detection unit
114 recording unit
115 display processing unit
321 first pressure sensor
322 second pressure sensor
323 first shielding plate
324 second shielding plate
325 first opening
326 second opening
327 first air port
331 first oscillation circuit
332 second oscillation circuit
401 branching air tube
500, 500A, 500B, 500C, 500D pressure sensor air tube
501 first air port connection head
502 second air port connection head
503 first connection tube
504, 510, 520, 530 second connection tube
505 protruding member

The invention claimed is:

1. An electronic sphygmomanometer comprising:
a cuff that is worn on a measurement area;
an inflation and deflation unit that adjusts a pressure applied to the cuff;
a pressure detecting unit comprising a first pressure sensor and a second pressure sensor, that detects a cuff pressure within the cuff based on pressure information outputted from the first pressure sensor and the second pressure sensor; and
a blood pressure calculation unit that calculates a blood pressure based on a change in the cuff pressure detected by the pressure detecting unit,
wherein the first pressure sensor and the second pressure sensor are disposed upon a first main surface of an internal circuit board,
wherein the first pressure sensor comprises a first air port that protrudes on a second main surface that is on an opposite side of the internal circuit board as the first main surface,
wherein the second pressure sensor comprises a second air port that protrudes on the second main surface of the internal circuit board,
wherein a pressure sensor air tube that allows the first air port and the second air port to communicate with each other is connected to the first air port and the second air port,
wherein a branching air tube that branches from a cuff air tube connected to the cuff is connected to the pressure sensor air tube, and
wherein the pressure sensor air tube comprises:
a first air port connection head connected to the first air port;
a second air port connection head connected to the second air port;
a first connection tube provided in the first air port connection head and to which the branching air tube is connected; and
a second connection tube that connects the first air port connection head and the second air port connection head,
wherein the second connection tube has a stress reduction function such that a thickness of a wall of the second connection tube is less than a thickness of a wall of the first connection tube, so that the stress of the second connection tube between the first air port connection head and the second air port connection head is reduced, and an elastomer is used for forming the first and second connection tubes,
wherein the wall of the first connection tube comprises a first inner wall delineated by a first inner diameter, wherein the wall of the second connection tube comprises a second inner wall delineated by a second inner diameter, and wherein the second inner diameter of the second connection tube is equal to the first inner diameter of the first connection tube.

2. The electronic sphygmomanometer of claim 1, wherein the wall of the first connection tube further comprises a first outer wall delineated by a first outer diameter, wherein the wall of the second connection tube further comprises a second outer wall delineated by a second outer diameter, and wherein the second outer diameter of the second connection tube is less than the first outer diameter of the first connection tube.

* * * * *